United States Patent [19]

Rosemeyer et al.

[11] Patent Number: 5,989,812
[45] Date of Patent: Nov. 23, 1999

[54] TRANSCRIPTION METHOD

[75] Inventors: Viola Rosemeyer, Wavre, Belgium; Rudolf Seibl, Penzberg, Germany

[73] Assignee: Boehringer Mannheim GmbH, Mannheim, Germany

[21] Appl. No.: 08/561,637

[22] Filed: Nov. 22, 1995

[30] Foreign Application Priority Data

Nov. 23, 1994 [DE] Germany ............... 44 41 602

[51] Int. Cl.⁶ .............. C12Q 1/68; C12P 19/34; C07H 21/02; C07H 21/04
[52] U.S. Cl. ............ 435/6; 435/91.1; 435/91.21; 536/24.1
[58] Field of Search ............ 435/6, 91.1, 91.21; 536/24.1; 935/77, 78

[56] References Cited

U.S. PATENT DOCUMENTS 5,474,916  12/1995  Reischl et al. ............... 435/91.2

FOREIGN PATENT DOCUMENTS

| A-0 396 775 | 5/1990 | European Pat. Off. . |
| WO 91/01384 | 2/1991 | WIPO . |
| WO-A-91 01384 | 2/1991 | WIPO . |
| WO-A-92 18521 | 10/1992 | WIPO . |

OTHER PUBLICATIONS

Sousa et al., "Model for the Mechanism of Bacteriophage T7 RNAP Transcription Initiation and Termination", *J. Mol. Biol.*, 224: 319–334, (1992).
Promega 1993/1994 Catalog, p. 110, 1993/94.
Goeddel, D. (Ed) "Gene Expression Technology" Academic Press, Inc. pp. 512–527, 1991.

*Primary Examiner*—Kenneth R. Horlick
*Attorney, Agent, or Firm*—Nikaido, Marmelstein, Murray & Oram LLP

[57] ABSTRACT

An improved method of transcribing nucleic acids wherein the amount of abortive transcripts formed is reduced wherein the improvement comprises an effector sequence in the transcription reaction.

20 Claims, 8 Drawing Sheets

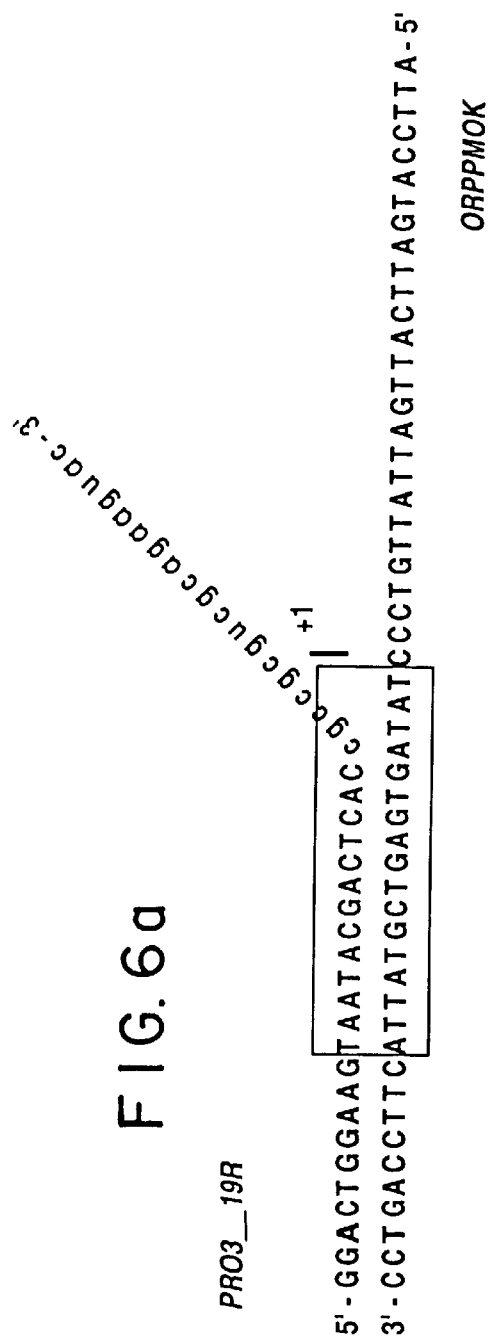
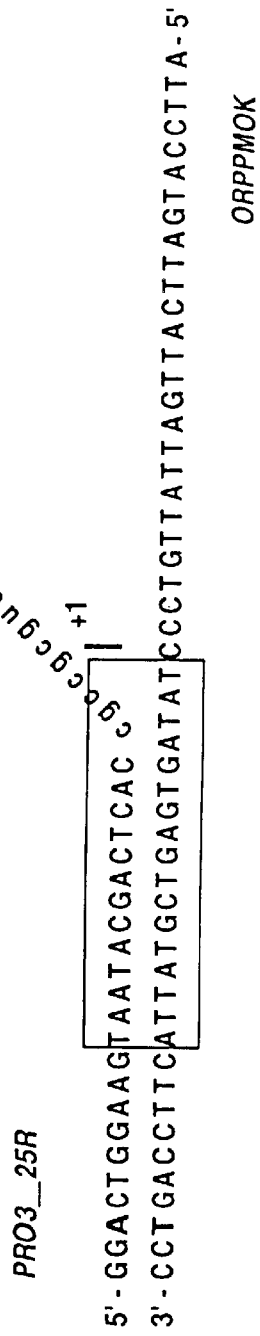

FIG. 6c

```
                                                      KOMP1_15R
                                    +1
PRO1                                |
5'- GGACTGGAAGTAATACGACTCACTATAGGGACAATAATCAATGAATCATGGAAT-3'
3'- CCTGACCTTCATTATGCTGAGTGATATCCCTGTTATTAGTTACCTTA-5'
         5'- cgccgcgucgcagaa                          ORPPMOK
```

FIG. 6d

```
                                                      PMOK4_21R
                                    +1
PROKOMP                             |
5'- GGACTGGAAGTAATACGACTCACTATAGGGACAATAATCAATGAATCATGGAAT-3'
3'- CCTGACCTTCATTATGCTGAGTGATATCCCTGTTATTAGTTACCTTA-5'
ORP4                                          guggggagugcgguggcgcg -3'
```

TRANSCRIPTION METHOD

Subject matter of the present invention are methods for transcribing a template nucleic acid sequence in a template nucleic acid into ribonucleic acid, suitable reagents, and advantageous applications and uses of these reagents.

In vitro transcription is a well accepted method for generating RNA molecules. In addition to the desired template sequence, which is hereinafter referred to as template nucleic acid sequence, this method requires an RNA polymerase and a promotor that is functionally linked to the template nucleic acid sequence. It is preferred to use RNA polymerases of the phages T3, T7, or SP6 as they are easy to handle and exhibit a high transcription efficiency. Template molecules, hereinafter referred to as template nucleic acids, are polynucleotides and oligonucleotides. Polynucleotides can be obtained, for example, via PCR or can be cloned in corresponding transcription vectors. The use of oligonucleotides, i.e. short nucleic acids, for the generation of RNA oligonucleotides is known.

EP-A-0408295 discloses a method for amplifying nucleic acids where a partially double-stranded nucleic acid is subject to a transcription reaction. The nucleic acid includes a DNA target sequence and a promotor nucleic acid, said promotor nucleic acid consisting of a promotor sequence, a sequence that is complementary to the target DNA, and a sequence that is complementary to the counter strand of the target DNA. From the reaction conditions, it can be concluded that the promotor nucleic acid is a DNA as the promotor nucleic acid would otherwise be digested by the RNase contained in the reaction mixture.

From J. Mol. Biol. 224, 319–334 (1992) it is known that in vitro transcription methods generate large amounts of abortive transcripts with a length of up to approximately 9 nucleotides. These short transcripts cannot be quantitatively separated by means of standard methods, e.g. precipitation by means of ethanol. Such a separation requires much more complex methods such as purification via HPLC or gel electrophoresis, for example. The abortive transcripts prevent the exact determination of the amount of full-length transcripts that were generated (e.g. via photometric measurement). Moreover, the generation of these abortive transcripts reduces the yield of full-length transcripts.

It was, hence, an object of the present invention to improve conventional transcription methods and reduce in particular the generation of abortive transcripts.

Subject matter of the invention is, hence, a method for transcribing a template nucleic acid sequence TN in a template nucleic acid T in ribonucleic acid R by forming a partially or completely double-stranded nucleic acid complex, said complex containing a functional, at least partially double-stranded promotor region of promotor sequences PP and PP', an effector sequence PE, and a template nucleic acid TN that is functionally linked to the promotor region and applying conditions under which the ribonucleic acid R is formed using TN as a template sequence under the control of the promotor.

The core of the invention is the finding that the amount of abortive transcripts that is generated can be reduced owing to the presence of an effector sequence PE (e.g. in the promotor region or at this region) without creating too much of a negative effect on the yield of full-length transcripts. This finding can principally be applied to all transcription methods provided they are carried out under the control of a promotor. This finding should be of particular importance for in vitro transcriptions and for transcriptions where phage RNA polymerases such as T7, T3, or SP6 are used.

Nucleic acids are understood to be both natural and synthetic nucleic acids. Natural nucleic acids are those occurring in viruses, bacteria, or multicellular organisms, for example. They contain, attached to a sugar phosphate backbone, nucleobases whose order at the backbone is characteristic for the respective organism or parts of its genome. An essential feature of nucleic acids is the capability of forming double strands with nucleic acids which possess a nucleobase sequence that is complementary thereto.

Synthetic nucleic acids are understood to be those whose structure has been modified, e.g. by replacing the sugar phosphate backbone with a polypeptide backbone or by introducing non-naturally occurring bases instead of the natural bases; the former, however, still have the capability of forming double strands with other nucleic acids, especially the natural nucleic acids.

Experts in the field understand transcription to be a procedure for generating ribonucleic acids with the aid of a template nucleic acid under the control of a promotor with an RNA polymerase.

A template nucleic acid T is a single or double-stranded or partially double-stranded nucleic acid which contains a template nucleic acid sequence TN to be transcribed into ribonucleic acid (R). The resulting ribonucleic acid is complementary to the template nucleic acid sequence. The strand containing the template nucleic acid sequence TN is known as the coding strand. The coding strand must be a deoxyribonucleic acid (DNA).

A promotor as understood in the present invention is an at least partially double-stranded nucleic acid region serving as a binding site for an RNA polymerase and as an initiation site for the transcription. When a template nucleic acid is attached to the promotor via the 5' end of the coding strand of the template, transcripts of the template nucleic acid sequence are synthesized provided suitable reaction conditions are set. Such a promotor is referred to as being functionally linked to the template nucleic acid sequence. The promoters used in the method of the present invention must be full length, but may contain nicks or small gaps. Examples show that the incorporation of nicks in the double strand of the promotor region has little or no influence on the efficiency of the transcription. When T7 promoters were used, it was possible to have nicks between positions -5/-4, -8/-7, -17/-11 of the non-coding strand and the positions -12/-13, -14/-15, and -15/-16 of the T7 promoter (FIG. 1). The promoters of the invention are partially double-stranded or fully double-stranded. It has been found that it is important that the non-coding strand PP of the promotor must reach approximately up to position -8, beginning from the 5' end, while the coding strand must reach approximately to position -13, beginning at the 5' end, without requiring that the following single stranded region be converted into a double strand by hybridization with another nucleic acid.

The coding strand of the promotor is hereinafter referred to as promotor sequence PP' while the non-coding strand is referred to as promotor sequence PP. The order of the nucleobases in the promotor region is known for a series of promoters from phages (e.g. T3, T7, or SP6).

Sequence PT designates a sequence that can be hybridized with a template nucleic acid. Sequence PT is, hence, essentially complementary to a part of the template nucleic acid. In a preferred manner, a longer template nucleic acid sequence follows this part of the template nucleic acid downstream of the promotor. This longer template nucleic acid is the subject matter of the transcription reaction, beginning with the part to which the sequence PT can be hybridized. The sequence PT is preferably not an RNA.

The effector sequence of the invention is also a nucleic acid. In a first, preferred aspect of the invention, the order of the nucleobases in the effector sequence is such that the selected conditions do not allow hybridization of the effector sequence with a template nucleic acid sequence TN, its counter strand TN', the promotor sequence PP or its counter strand PP'. In a preferred manner, the effector sequence should not hybridize with other nucleic acids present in the reaction mixture. A second aspect of the invention proposes that the effector sequence be preferably not a DNA since the total efficiency of the transcription reaction is negatively affected if the effector sequence is a DNA.

The length of the effector sequence PE is largely irrelevant. Experience showed, however, that it should have a minimum length of 4 nucleotides. A preferred length of the PE is 5–50, a particularly preferred length 10–30 nucleotides.

A promotor nucleic acid P is understood to be a nucleic acid which contains either a promotor sequence PP and/or its counter strand PP' in addition to other nucleic acid sequences.

A linker is understood to be a part of a molecule which contains one or several atoms and covalently links two nucleic acid sequences to each other. The linker can be one of a nucleoside origin or also of a non-nucleoside origin. In a preferred manner, the linker is a nucleic acid sequence. In one embodiment, the linker is a sequence PT which can be hybridized with the template nucleic acid sequence.

In another embodiment, the linker is any desired connection between a promotor strand and the effector sequence.

BRIEF DESCRIPTION OF THE DRAWING

FIG. 6, shows the oligonucleotides and their sequences used in the examples.

FIG. 1 shows a model nucleic acid (double-stranded, SEQ. ID. NO. 10), showing the tolerance for nicks.

Figure 2:
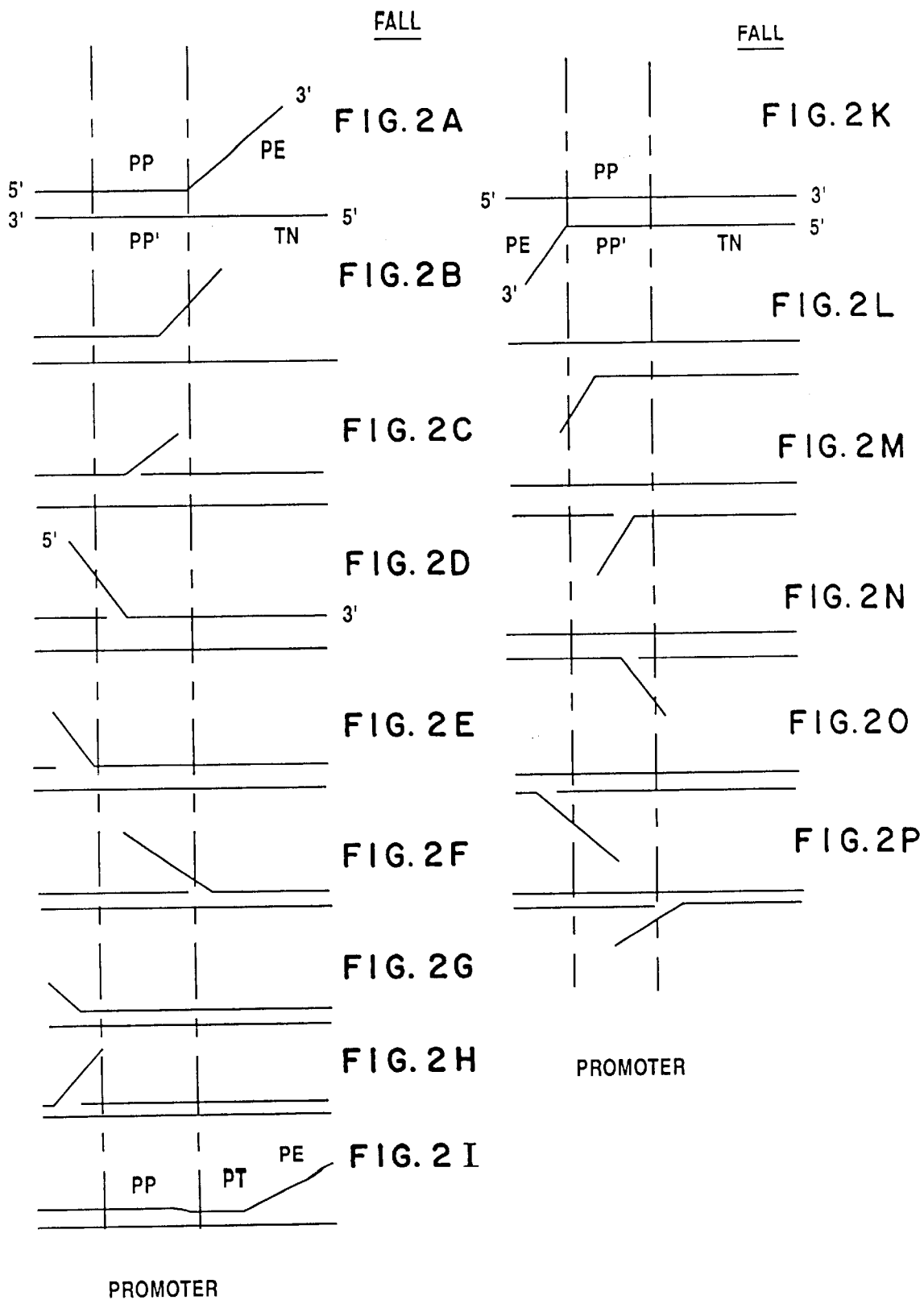
FIGS. 2A–2P show how the link between the effector sequence and the promoter sequence can be accomplished.

The link between the effector sequence and the promotor sequence can be accomplished in several different ways. One of these cases is shown in FIG. 2. In a first possibility, the effector sequence PE is coupled to the 3' end of the promotor sequence PP either directly or via a linker.

In a second case (case A of FIG. 2), the effector sequence is directly linked to the nucleotide in position -1 of the promotor sequence PP. This can be achieved in a simple manner via a conventional phosphodiester binding between a 3' hydroxyl group of the promotor sequence and a 5' hydroxyl group of the effector sequence.

In a third embodiment (case B in FIG. 2), the effector sequence is linked directly to a 3' hydroxyl group of a promotor sequence PP which, as compared to the complete promotor sequence, can be truncated from position -1 to position -8 (in case a T7 promotor is used). In this case, it is not necessary to use a second molecule which contains the promotor nucleotides that are not contained in PP.

In a fourth embodiment, the effector sequence is linked to a 3' hydroxyl group of the promotor sequence PP; this 3' end is located approximately between nucleotide -9 and the 5' end of the promotor region (if a T7 promotor is used). In this case, it is necessary to have a second promotor sequence which is separate from PP, said sequence containing the promotor nucleotides that are not contained in PP (case C of FIG. 2).

In a fifth embodiment, the 3' end of the effector sequence is linked to a 5' hydroxyl group of a nucleotide in the promotor sequence PP. This position is located downstream of position -12. In this case, it is also preferred to have the second promotor oligonucleotide which contains the promotor nucleotides that are not contained in PP (case D of FIG. 2).

In a sixth embodiment (case E of FIG. 2), the effector sequence PE is linked directly to the 5' end of the promotor sequence PP.

Additional possibilities are illustrated in cases F–I shown in FIG. 2.

The above listed embodiments can be correspondingly applied to the coding strand of the promotor, the promotor sequence PP'; however, the above listed tolerance limits of the promotor sequence PP' must be taken into consideration.

In a first embodiment (case K of FIG. 2), the effector sequence PE is linked to the 3' hydroxyl group of the coding strand of the promotor region PP'.

In a second embodiment (case L of FIG. 2), the effector sequence PE is linked to a 3' end of PP' in such a manner that only the nucleotides -1 to approx. -14 or more of the sequence PP' are present. In this case it is not necessary to have an additional oligonucleotide for single-stranded regions.

In a third embodiment (case M in FIG. 2), the 5' end of the effector sequence is linked to the 3' end of the coding strand of the promotor region in such a manner that the strand of the promotor region which contains the effector sequence contains only the nucleotides between position -1 and position approx. -12. This case requires the use of an additional oligonucleotide.

In a fourth embodiment (N), the 3' end of the effector sequence is bound to the 5' end of the strand PP' within the promotor. In this case it is also recommended that the single-stranded segments be covered with an oligonucleotide or that the extended template nucleic acid sequence by means of hybridization.

In a fifth embodiment (O), a 5' end of a strand is linked to the 3' end of the effector sequence such that a coding strand, linked to the target sequence, covers the entire promotor sequence.

In a sixth embodiment (P), the effector sequence is bound to the 3' end of the template nucleic acid sequence such that the coding strand of the promotor is completely retained and not bound to a template sequence.

To date, an embodiment where the 3' end of the effector sequence is linked to the 5' end of the promotor region on strand PP', could not be used for transcription.

In each of these cases, it is, however, also possible that the 5' end of PP and/or the supplementary oligonucleotide be coupled to the 3' end of PP' or the supplementary oligonucleotide either directly or via a linker with the aid of a loop structure. In a preferred manner, the left ends of each case in FIG. 2 are coupled via a linker of 5–40 nucleotides in length.

The transcription method of the invention requires all reaction conditions that are generally necessary for transcription reactions. They include especially a DNA-dependent RNA polymerase (transcriptase). The latter synthesizes numerous RNA copies of the template nucleic acid sequence TN while it is irrelevant whether the sequence is single-stranded or double-stranded, e.g. present in a larger template nucleic acid. The RNA molecules are formed in 3' direction beginning at the starting position of the promotor. The promotor sequence is not transcribed. The transcriptase must match the promotor used. When a typical promotor of the bacteriophage T7 is used, it is also necessary to use a T7-RNA polymerase.

Another absolutely necessary part of a transcription reaction are monoribonucleoside triphosphates (rNTP). They are attached to the resulting ribonucleic acids by means of the polymerase. These rNTPs can be unmodified, but also modified, e.g. by attaching labeling groups.

A labeling as understood in the present invention is a group L which can be detected either directly or indirectly. Directly detectable groups include radioactive ($^{32}P$), dyed, or fluorescent groups or metal atoms. Indirectly detectable groups include immunologically or enzymatically active compounds such as antibodies, antigens, haptens, or enzymes or enzymatically active partial enzymes. They are detected in a subsequent reaction or reaction sequence. Haptens are particularly preferred as the nucleoside triphosphates where they are used as labels are generally particularly well suited as substrates of polymerases; a subsequent reaction with a labeled antibody to the hapten or the haptenized nucleoside is then easy to accomplish. Such nucleoside triphosphates include bromonucleoside triphosphates or digoxigenin, digoxin, biotin or fluorescein coupled nucleoside triphosphates. The steroids and their detection as described in EP-A-0 324 474 have proven to be particularly suitable. For details on their incorporation in nucleic acids, refer to EP-A-0 324 474.

In a first, particularly simple embodiment of a transcription reaction to generate ribonucleic acids from template nucleic acids that are naturally single-stranded or rendered single-stranded, this template nucleic acid T is brought into contact with a promotor nucleic acid P; the latter contains the promotor sequence PP, the sequence PT which can be hybridized with the template nucleic acid sequence, and the effector PE. The contact is accomplished under hybridization conditions. These conditions can already be set such that the transcription reaction can occur after formation of the hybrid. It is, however, also possible to adjust the conditions only after hybridization in order to start the transcription reaction. The sequences PP' necessary for transcription are also contained in T or are added. A large number of transcripts is formed after a sufficient waiting period. These transcripts can be used for any further treatment or use.

The possibility for further treatment is the cyclic amplification of this ribonucleic acid. For this purpose, the ribonucleic acid can be hybridized with an further primer PR whose sequence is selected such that its extension leads to a nucleic acid which contains a part which in turn can be hybridized with the part PT of the promotor nucleic acid P. This reaction requires the reagents usually necessary for cDNA synthesis, e.g. a reverse transcriptase and deoxyribonucleoside triphosphates (dNTP). In order to accomplish amplification, the ribonucleic acid and the extension product must be separated from PR or the ribonucleic acid must be digested. The second possibility, in particular when using RNAse H, is particularly advantageous as it allows an isothermal cyclic reaction. Once present as a single strand, the extension product of the primer can hybridize with the promotor nucleic acid. Under the reaction conditions, the 3' end of the extension product can then be extended by the coding strand PP'. The so formed partial double-stranded nucleic acid can again be used for transcription in order to generate RNA. Both the number of extension product and the amount of ribonucleic acid present in the reaction mixture increase with the number of reaction cycles carried out.

Figure 3:
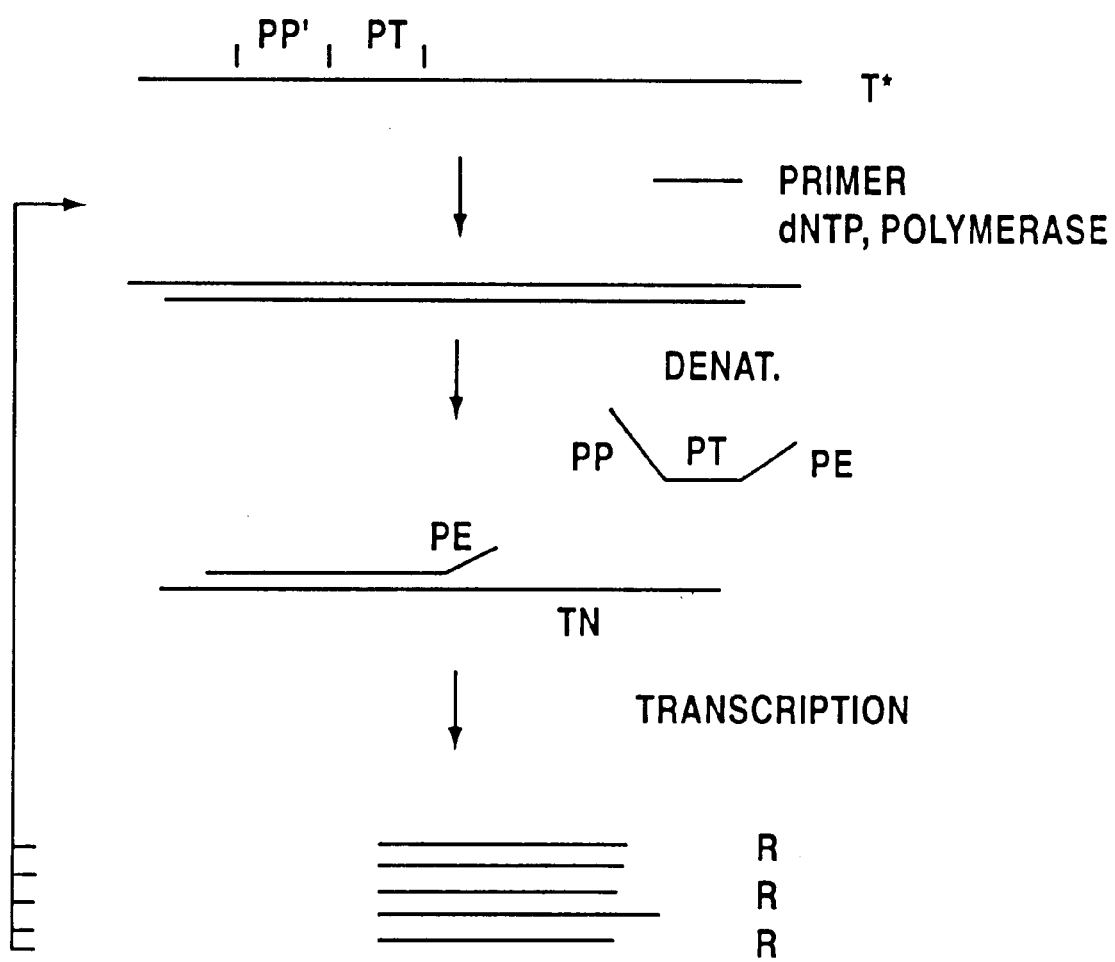
FIG. 3 shows another embodiment of the method of the invention.

In another embodiment of the method of the invention as shown in FIG. 3, the partially double-stranded nucleic acid complex is formed in a pre-reaction. A single-stranded template nucleic acid T*, which is a precursor to the template nucleic acid used in the transcription reaction, which can be both DNA or an RNA in this embodiment, is hybridized with a primer. dNTPs and a polymerase enzyme that is dependent on the type of template nucleic acid are used to extend the primer to form an extension product; the latter then serves as a template nucleic acid. Attention must be paid to the fact that the primer is selected such that its extension product is the template nucleic acid sequence TN. It must also contain a sequence that can be hybridized with the sequence PT. PT is not required when PP' is contained in T*. The extension product of the primer must now be made available in a single-stranded form. This can be accomplished either by denaturing (especially when DNA is used as a template nucleic acid T*) or by means of treatment with RNAse H (when the template nucleic acid T* is an RNA). Subsequently, the extension product of the primer is hybridized with the promotor nucleic acid P which contains the components PP', PT, and PE in this order. Subsequently, the transcription reaction is allowed to occur. It is again possible to cyclically amplify the so formed RNA while again using alternatingly the primer and the promotor nucleic acid P. The so formed RNA is then again used as a template nucleic acid T*.

Prior art knows a series of amplification methods where promotor nucleic acids are used. In all these methods, the formation of abortive transcripts is still a problem. These methods can be improved with the aid of the present invention in that the promotor nucleic acid sequences in accordance with the invention are used as promotor nucleic acids. Examples for said known methods are described in EP-A-0408295, PE-A-0329822, WO 90/01068, PE-A-0373960, EP-A-0397269 and EP-A-0369775.

Figure 4:
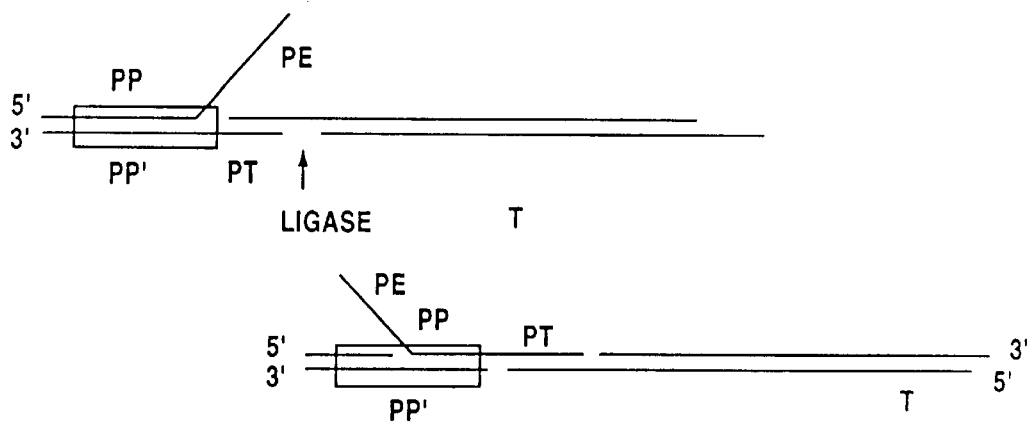
FIG. 4 shows a third embodiment of the method of the invention.

In a third embodiment (FIG. 4), a partially double-stranded nucleic acid (e.g. DNA), which has a single-stranded region, is used as a template nucleic acid T. This type of template nucleic acids are, for example, fragments of double-stranded nucleic acids that are obtained by digestion with restriction enzymes while generating overlapping ends. Such an overlapping end of the template nucleic acid serves to hybridize with the template-specific segment PT of a partially double-stranded promotor nucleic acid P. The promotor nucleic acid contains in a first strand the promotor sequence PP to which the effector sequence is coupled either directly or via a linker at the 3' end or within the promotor sequence. Moreover, the promotor nucleic acid P contains on another strand the promotor sequence PP' and, in 5' direction, the template-specific sequence PT. A complex of promotor nucleic acid and template nucleic acid then forms under hybridization conditions. If desired, the 5' end of the template-specific sequence can be covalently coupled by means of a ligase to the 3' end of the template nucleic acid located in its vicinity. Subsequently, the nucleic acid complex is available for generating transcripts. The sequence PT can be located correspondingly at the 3' end of PP and PT is complementary to parts of TN or to TN in its entirety.

Figure 5:
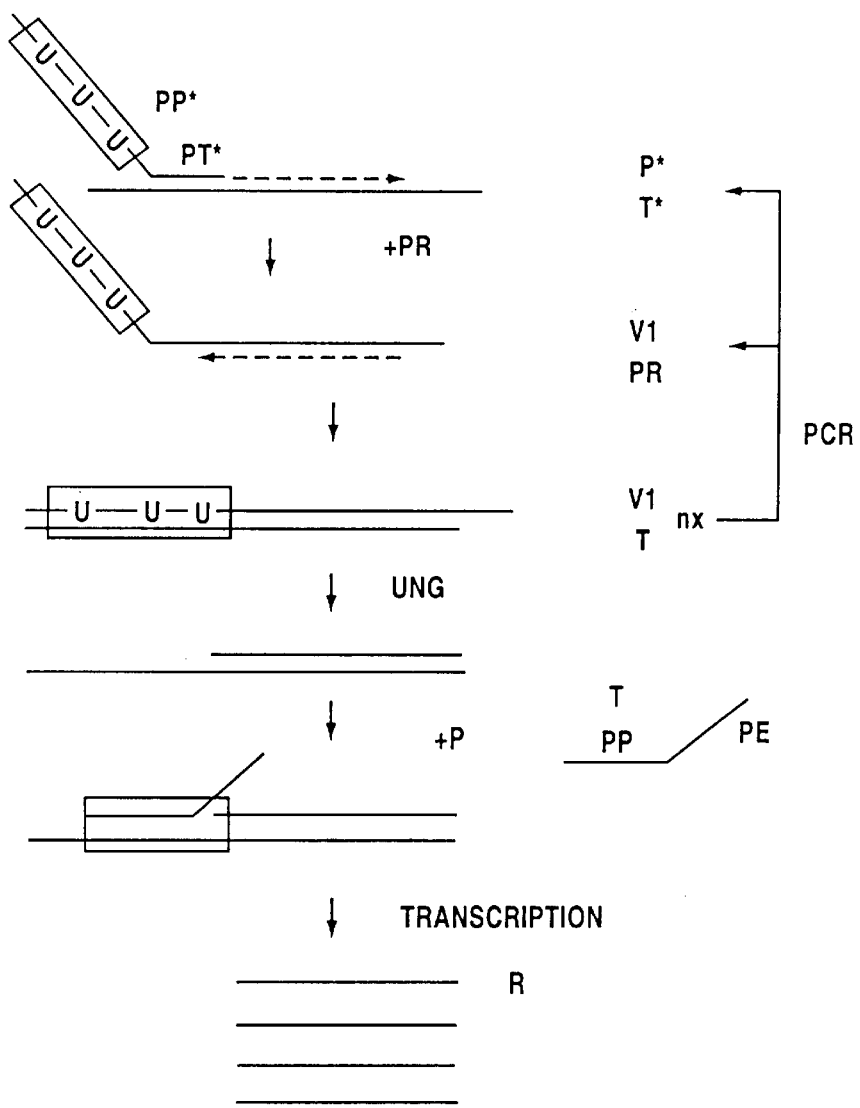
FIG. 5 shows a fourth embodiment of the method of the invention.

In a fourth embodiment (FIG. 5), a quite similar nucleic acid complex is obtained without requiring cleavage by means of restriction enzymes. A desired template nucleic acid T which is naturally single-stranded or rendered single-stranded, is reacted with the first promotor nucleic acid P* containing a digestible promotor sequence PP* where e.g. thymine bases are at least partially replaced by uracil bases; and at the 3' end of the promotor sequence there is a first primer sequence PT* which is complementary to the template nucleic acid. Under conditions used for the polymerase chain reaction (EP-A-0202184), i.e. using another primer PR that is partially complementary to the extension product V1 formed with the aid of the first primer, a double-stranded nucleic acid is formed which contains the double-stranded promotor sequence at its one end and the double-stranded sequence of the second primer at its other end. The extension product of the primer PR later serves as the template nucleic acid T. By treatment with uracil-N-glycosilase, the promotor sequence PP* is digested. The nucleic acid which is now partially single-stranded in the promotor segment, is hybridized with the promotor nucleic acid P that is partially or completely single-stranded in accordance with the invention; said promotor nucleic acid P contains a promotor sequence PP that is complementary to the single-stranded segment and, bound directly thereto, an effector sequence PE. The so formed nucleic acid complex is again available for transcription.

Another subject matter of the invention are promotor nucleic acids which contain a promotor sequence PP and/or its counter strand PP', and an effector sequence PE that is not a DNA. The promotor sequences PP and PP' differ from the effector sequence PE with respect to the components of which they are made. The promotor sequences PP or PP' DNA are preferred. The promotor nucleic acid is preferably a single-stranded molecule, but can also be double-stranded. When double-stranded molecule is used, the promotor nucleic acid contains both PP and PP* or parts thereof so that the promotor region formed therewith is fully functional.

As already described for cases A to E and G (FIG. 2), the sequences PP and PE are preferably located on one strand. If the promotor nucleic acid also contains a template-specific sequence PT, the latter is also preferably located on the same strand as PP and PE and/or PP' and PE (case G).

In cases K, L, and N of FIG. 2, PP' and PE are preferably located on one strand.

Another subject matter of the invention are reagent kits which contain all reagents necessary for the transcription reaction that is to be carried out; except for the template nucleic acid from which the transcripts are to be made. The kits contain at least one promotor nucleic acid P.

Another subject matter of the invention is the use overhanging sequences, especially RNA on promotor sequences to reduce the formation of abortive transcripts, improve the quantitative determination of nucleic acid products in transcription methods, increase the sensitivity in the detection of nucleic acids and/or reduce the amount of mononucleotides required in transcription reactions.

The reduction of the amount of abortive transcripts in accordance with the invention significantly improves known transcription methods. The overhanging sequences in particular improve the quantitative determination of nucleic acid products in transcription methods. Such a determination has so far been difficult considering that the amount of abortive transcripts formed ranged in an order of magnitude of up to 80% of all transcripts formed. In accordance with the invention, the method of the invention can also be used to increase the sensitivity of nucleic acid determinations in transcription methods as the resulting abortive transcripts lead to a background signal for the determination of full-length transcripts which is now reduced. The generation of abortive transcripts also entails an increased requirement of rNTPs which are then not available for the generation of full-length transcripts. With the invention it is possible to use a smaller number of ribonucleotides. Moreover it is also conceivable that the amount of formed full-length transcripts is increased while the amount of rNTP remains the same.

The present inventors have found that DNA overhangs rather than RNA overhangs cause the amount of total transcripts to be reduced if not completely eliminated, dependending on the length of the DNA overhangs. Applicants have found that the complete substitution of the effector sequences of the invention with DNA overhangs generally did not lead to the effects of the invention.

Although it was not possible to name a cause for the effect of the invention with certainty, it appears to be conceivable that RNA polymerases, like the T7-RNA polymerase that was examined, can be converted from an abortive into a processive form by means of an RNA overlap at or in the promotor region.

FIG. 6 shows the oligonucleotides and their sequences used in the examples. The deoxyribonucleotides are designated with upper case letters while the ribonucleotides are designated with lower case letters. All oligonucleotides are linear and single-stranded.

The following examples illustrate the invention in greater detail:

EXAMPLE 1

A reaction mixture A and a reaction mixture B were obtained by adding all components listed in Table 1. Mixture A contains all characteristics of mixture B with the exception of the effector sequence PE.

TABLE 1

| 20 µl | A (µl) | B (µl) |
|---|---|---|
| PRO319R (10 pmol/µl) (SEQ.ID.NO. 1) | — | 1 |
| PRO3 (10 pmol/µl) (SEQ.ID.NO. 2) | 1 | — |
| ORPPMOK (10 pmol/µl) (SEQ.ID.NO. 3) | 1 | 1 |
| 10 mM ATP, CTP, GTP, UTP | 2 | 2 |
| 10 × transcription buffer | 2 | 2 |
| 1% Triton | 0.5 | 0.5 |
| Rnasin (40 U/µl) | 0.5 | 0.5 |
| $H_2O$ | 11 | 11 |
| T7-Pol (700 U/µl) | 1 | 1 |
| α-[$^{32}$P]-CTP | 1 | 1 |

PRO3: 5'-GGACTGGAAGTAATACGACTCAC-3' (SEQ.ID.NO. 2)
10 × transcription buffer:

| 400 | mM | Tris (pH 7.9) |
| 60 | mM | $MgCl_2$ |
| 100 | mM | DTT |
| 20 | mM | Spermidin |

The above listed mixtures were incubated at 37° C. After 5, 10, 15, 30 and 60 min, portions of 4 µl were removed, and the reaction was stopped using 3 µl of application buffer for a sequence gel.

Figure 7:
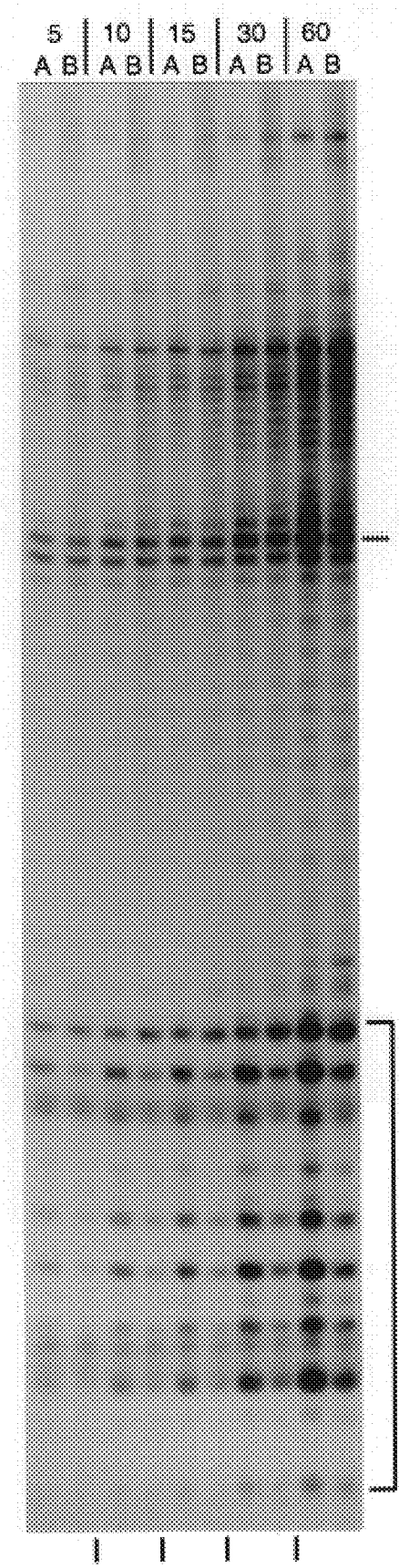
FIG. 7 shows a autoradiograph of the gel in example 1.

In order to determine the relative amounts of transcripts produced, a determination was carried out in a 20% sequencing gel (according to Sambrook et al. (1989) Molecular Cloning, CSH Laboratory Press pp 6.36 et seq.). Portions of 3 μl after denaturing were applied. A voltage of 2300 volts was applied. An autoradiograph of the gel was obtained (FIG. 7). As opposed to the gels shown in EP-A-408295, this representation also shows areas where the short transcripts are visible. It can be clearly seen that the amount of abortive transcripts in mixture B is greatly reduced as compared to mixture A.

The procedure described in this example can be used as a general working instruction for the transcription with the aid of the promotor nucleic acids in accordance with the invention.

This example shows that the effector sequence PE can be coupled to the 3' end of the promotor sequence PP even when this end is within the promotor region and the noncoding strand of the promotor sequence is not complete. In the present case, the positions -1 to 4 of the non-coding strand of the promotor region are not shown as the 5' end of the effector sequence is coupled to the 3' hydroxyl group of the nucleotide in position -5 (cytosine).

EXAMPLE 2

The invention was further tested in other embodiments using the instructions given in example 1.

a) Instead of the nucleic acids listed in example 1, an embodiment which corresponds to the above listed embodiment 5 (case D of FIG. 2) was used where the effector sequence was bound to the 5' end of the promotor sequence PP within the promotor region. The promotor region is understood to be the consensus sequence of the T7-RNA polymerase promoters. The so generated promotor nucleic acid P is termed KOMP1_15R (SEQ. ID. NO. 4). This promotor nucleic acid contains the positions -1 to -11 of the promotor region of T7. Moreover, another oligonucleotide identified as PRO1 (SEQ. ID. NO. 5) was added to the reaction mixture; said oligonucleotide contains the positions -12 to -17 of the non-coding strand of the promotor region and also additional nucleotides that are complementary to the template nucleic acid T. An oligonucleotide designated as ORPPMOK (SEQ. ID. NO. 3) was used as a template nucleic acid; it contains the template nucleic acid sequence, a promotor sequence PP', and another segment that is complementary to oligonucleotide PRO1 (SEQ. ID. NO. 5).

b) Another embodiment, case M of FIG. 2, showed that it is also possible to bind the effector sequence PE to a position within the coding strand of the promotor region. In the present case, PE was bound to guanosine in position -12 of the promotor region. The so formed promotor nucleic acid contains, beginning from the 3' end, the effector sequence PE, a promotor sequence PP' and a template nucleic acid TN. This promotor nucleic acid is designated as PMOK4_21 R (SEQ. ID. NO. 6). Moreover, an oligonucleotide ORP4 is added to the reaction mixture; this oligonucleotide has at its 5' end the remaining 5 nucleotides of the coding strand of the promotor region and additional nucleotides that are complementary to a strand identified as PROKOMP (SEQ. ID. NO. 7). In order to keep these oligonucleotides together and render the promotor region functional, the oligonucleotide PROKOMP is added which is complementary to the 3' end of ORP4 (SEQ. ID. NO. 8), if looked at from the 5' end, and the noncoding strand of the promotor region and then a sequence that is complementary to the template nucleic acid.

c) In another example which mentions the selection of the template nucleic acid and the promotor sequence PP of example 1, the effect of the effector sequence length was tested. While the effector sequence of example 1 has a length of 19 ribonucleotides, PRO3_25R (SEQ. ID. NO. 9) contains an effector sequence with a total length of 25 ribonucleotide units. This demonstrates that the length of the effector sequence, at least in the segments shown, has no relevant influence on the effect of the invention.

In FIG. 6, ribonucleotides are indicated in lower case letters while deoxyribonucleotides are given in upper case letters. The consensus sequence of the promotor was marked with a frame rounded and the transcription start was designated with +1.

Figure 8A:
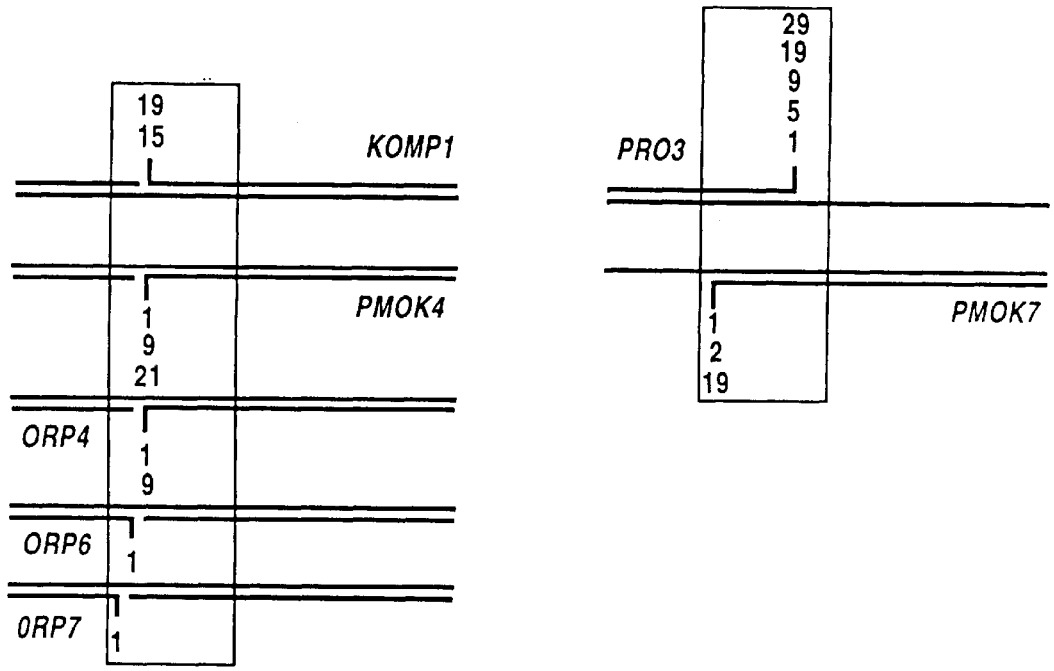
FIGS. 8A and 8B are a diagrammatic representation showing the effect of position and length of DNA overhang in the promoter region.
Figure 8B:
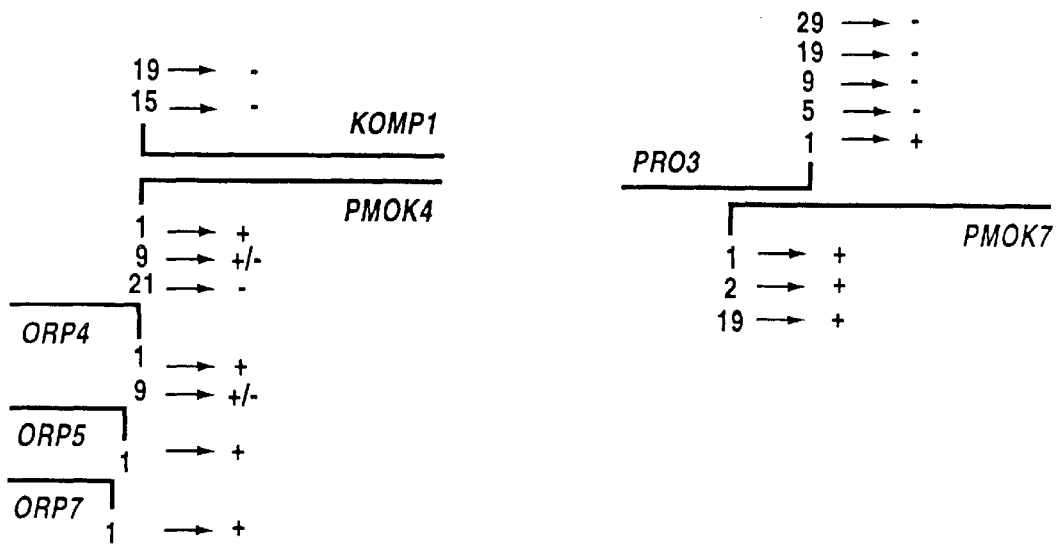

FIG. 8B is a diagrammatic representation showing the effect of position and length of DNA overhangs in the promotor region. The hatched segment (FIG. 8A) indicates the promotor region. The numbers at the vertical lines indicate the number of nucleotides that make up the overhangs. "+" indicates that an efficient transcription took place; "−" means that the transcription was completely inhibited by the DNA overhangs; "+/−" indicates a reduced efficiency (FIG. 8B).

EXAMPLE 3

Figure 1:
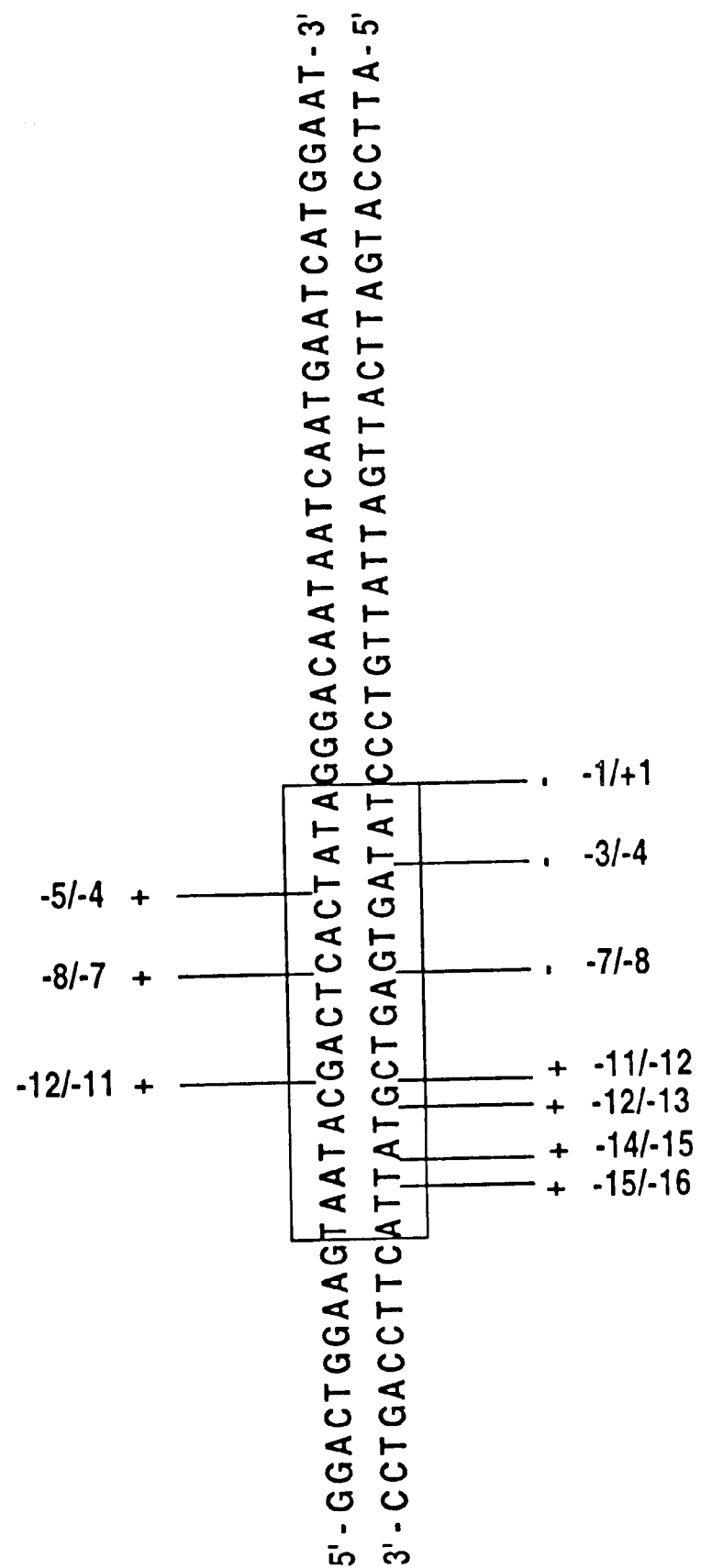
FIG. 1 shows a model nucleic acid, showing the tolerance for nicks.

In another example, the effect of a nick on the promotor region was tested. FIG. I shows whether a nick and a missing phosphate group between the indicated nucleotide positions in the coding and/or non-coding strand of the promotor region were tolerated (+) or not tolerated (−) (FIG. 1).

We claim:

1. A method for transcribing a template nucleic acid sequence TN in a template nucleic acid T into ribonucleic acid R comprising:

a) providing a partially or completely double-stranded nucleic acid complex, comprising:
      i) a functional, double-stranded or partially double-stranded phage promoter region consisting of promotor sequences PP and PP',
      ii) a single-stranded effector sequence PE which does not hybridize to any of PP, PP', or TN, wherein PE is covalently bound to PP or PP' in any order, and
      iii) a template nucleic acid sequence TN that is functionally linked to the promotor region, and
   b) providing reagents and conditions necessary for transcription such that ribonucleic acid R is formed with TN as a template under the control of the promoter.

2. The method of claim 1, wherein the effector sequence PE is linked to the promoter region either directly or via a linker.

3. The method of claim 1 wherein PE is bound at the end of or within PP or PP'.

4. The method of claim 1 wherein PE cannot hybridize with a sequence selected from the group consisting of the template nucleic acid sequence TN, the complementary strand TN', and the promoter sequences PP and PP', under the transcription reaction conditions.

5. The method of claim 1 wherein PE is RNA.

6. The method of claim 1 wherein the promoter region further comprises a sequence PT that can be hybridized with at least a part of the template nucleic acid.

7. The method of claim 1, wherein the template nucleic acid sequence TN or TN' is part of a nucleic acid with a single-stranded or double-stranded region, while a sequence PT is or can be hybridized to the single-stranded region of the template nucleic acid.

8. The method of claim 1, wherein the template nucleic acid sequence TN is covalently linked to the promotor sequence PP'.

9. The method of claim 1, wherein the effector sequence PE is located at the 3' end of the promotor sequence PP.

10. The method of claim 1, wherein the effector sequence PE is neither complementary nor sequence-identical to a part of the template nucleic acid T.

11. The method of claim 1, wherein the effector sequence PE has a minimum length of 4 nucleotides.

12. The method of claim 1, wherein the effector sequence PE has a minimum length of 9 nucleotides.

13. The method of claim 1, wherein the effector sequence PE is at least partially RNA.

14. The method of claim 1 further comprising, before step a):
   1) providing a first single-stranded template nucleic acid T* which is hybridized to a first promoter nucleic acid P* which contains a degradable promoter sequence PP* and a sequence PT* that can be hybridized with the template nucleic acid T*,
   2) extending the promoter nucleic acid P* using the template nucleic acid T* as a template to form an extension product V1,
   3) forming a strand that is complementary to the extension product V1,
   4) degrading the promoter sequence PP*,
   5) using the resulting complementary strand as template nucleic acid T in the method of claim 1.

15. A promotor nucleic acid containing a phage promoter sequence PP or its complementary strand PP' and a single-stranded effector sequence PE, wherein the sequence PE does not hybridize to PP or PP', and is not DNA.

16. The promotor nucleic acid of claim 15, further comprising the respective complementary strand PP' or PP.

17. The promotor nucleic acid of claim 15, further comprising a template-specific sequence PT.

18. The promotor nucleic acid of claim 17, wherein the template-specific sequences PT is located on the same strand as PP and PE.

19. The promotor nucleic acid of claim 17, wherein PT is located on the complementary strand to PP and PE.

20. A method for detecting a template nucleic acid, comprising
   1) providing a template nucleic acid T containing a sequence TN,
   2) transcribing said template nucleic acid sequence TN using the method of claim 1, and
   3) detecting the template nucleic acid by the presence of the ribonucleic acid R formed in the transcription reaction.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "OTHER NUCLEIC ACID"

(xi) SEQUENCE DESCRIPTION: SEQ ID NO:1:

```
GGACTGGAAG TAATACGACT CACCGCCGCG UCGCAGAAGA UC                42
```

(2) INFORMATION FOR SEQ ID NO:2:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID"

(xi) SEQUENCE DESCRIPTION: SEQ ID NO:2:

```
GGACTGGAAG TAATACGACT CAC                                    23
```

(2) INFORMATION FOR SEQ ID NO:3:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID"

(xi) SEQUENCE DESCRIPTION: SEQ ID NO:3:

```
ATTCCATGAT TCATTGATTA TTGTCCCTAT AGTGAGTCGT ATTACTTCCA GTCC    54
```

(2) INFORMATION FOR SEQ ID NO:4:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID"

(xi) SEQUENCE DESCRIPTION: SEQ ID NO:4:

```
CGCCGCGUCG CAGAAGACTC ACTATAGGGA CAATAATCAA TGAATCATGG AAT     53
```

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID"

(xi) SEQUENCE DESCRIPTION: SEQ ID NO:5:

```
GGACTGGAAG TAATAC                                            16
```

(2) INFORMATION FOR SEQ ID NO:6:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID"

(xi) SEQUENCE DESCRIPTION: SEQ ID NO:6:

```
ATTCCATGAT TCATTGATTA TTGTCCCTAT AGTGAGTCGC GCCGCGUCGC AGAAGAUCUC        60

(2) INFORMATION FOR SEQ ID NO:7:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID"

(xi) SEQUENCE DESCRIPTION: SEQ ID NO:7:

GGACTGGAAG TAATACGACT CACTATAGGG ACAATAATCA ATGAATCATG GAAT              54

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID"

(xi) SEQUENCE DESCRIPTION: SEQ ID NO:8:

TATTACTTCC AGTCC                                                         15

(2) INFORMATION FOR SEQ ID NO:9:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID"

(xi) SEQUENCE DESCRIPTION: SEQ ID NO:9:

GGACTGGAAG TAATACGACT CACCGCCGCG UCGCAGAAGA UCUCAAUC                     48

(2) INFORMATION FOR SEQ ID NO:10:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OTHER NUCLEIC ACID"

(xi) SEQUENCE DESCRIPTION: SEQ ID NO:10:

GGACTGGAAG TAATACGACT CACTATAGGG ACAATAATCA ATGAATCATG GAAT              54
```